(12) United States Patent
Hou et al.

(10) Patent No.: US 11,534,485 B2
(45) Date of Patent: Dec. 27, 2022

(54) VACCINE USED FOR PREVENTING TOXOPLASMA GONDII INFECTION AND PREPARATION METHOD THEREFOR

(71) Applicant: Haimu Animal Health Products (Shandong) Co., Ltd., Zaozhuang (CN)

(72) Inventors: Feng Hou, Teda Tianjin (CN); Lili Cao, Teda Tianjin (CN); Pengtao Gong, Teda Tianjin (CN); Siming Li, Teda Tianjin (CN); Xingyuan Chen, Teda Tianjin (CN); He Ding, Teda Tianjin (CN); Dian Wang, Teda Tianjin (CN)

(73) Assignee: Haimu Animal Health Products (Shandong) Co., Ltd.

( * ) Notice: Subject to any disclaimer, the term of this patent is extended or adjusted under 35 U.S.C. 154(b) by 0 days.

(21) Appl. No.: 17/253,798

(22) PCT Filed: Oct. 22, 2018

(86) PCT No.: PCT/CN2018/111235
§ 371 (c)(1),
(2) Date: Jul. 15, 2021

(87) PCT Pub. No.: WO2019/242177
PCT Pub. Date: Dec. 26, 2019

(65) Prior Publication Data
US 2022/0040273 A1    Feb. 10, 2022

(30) Foreign Application Priority Data

Jun. 19, 2018  (CN) .......................... 201810632019.6

(51) Int. Cl.
| A61K 39/002 | (2006.01) |
| A61P 33/02 | (2006.01) |
| C07K 14/45 | (2006.01) |
| A61K 39/00 | (2006.01) |

(52) U.S. Cl.
CPC ............ *A61K 39/002* (2013.01); *A61P 33/02* (2018.01); *C07K 14/45* (2013.01); *A61K 2039/521* (2013.01); *A61K 2039/552* (2013.01); *C07K 2319/00* (2013.01)

(58) Field of Classification Search
None
See application file for complete search history.

(56) References Cited

U.S. PATENT DOCUMENTS

| 2006/0148696 A1 | 7/2006 | Aliberti et al. |
| 2009/0208519 A1 | 8/2009 | Tuo et al. |

FOREIGN PATENT DOCUMENTS

| CN | 106397563 A | 2/2017 |
| CN | 111234035 A | 6/2020 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
GenBank, "Toxoplasma Gondii Rh 18 kDa Cyclophilin mRNA, complete cds"; May 11, 1994.
Gong Shouliang, "Radiation Therapy of Tumor Genes"; People's Military Medical Publishing House; Beijing; Sep. 2013; ISBN 978-7-5091-6698-7.
High KP et al. "Isolation, cDNA Sequences, and Biochemical Characterization of the Major Cyclosporin-Binding Proteins of Toxoplasma Gondii"; The Journal of Bilogical Chemistry, vol. 269, No. 12, Mar. 25, 1994; pp. 9105-9112, see Fig. 6.
Huang Jin-gui, et al. "Studies on Immuno-Protection from a Toxoplasma Gondii Infection Provided by a TgCyP Subunit Vaccine"; Journal of Pathogen Biology; Jul. 31, 2011; vol. 6, No. 7; pp. 517-520, see abstract and section 2.
Li Yunna, et al. "Construction of the Eukaryotic Expression Plasmid of TgCyP Gene from Toxoplasma gondii and its Expression in Hella Cells"; Genomics and Applied Biology; 2011; vol. 30, No. 4, 311-315.
Li Yunna, et al. "Cloning and Prokaryotic Expression of Cyclophilin Gene of Toxoplasma Gondii"; Chinese Journal of Bilogicals; vol. 23, No. 9; Sep. 30, 2010; pp. 961-966; see abstract and sectiosn 1.6-1.11.
Gong P. et al, "The protective effect of a DNA vaccine encoding the Toxoplamsa gondii cyclophilin gene in BALB/c mice", Parasite Immunology, vol. 35, No. 3-4, 5, Feb. 2013, pp. 140-146.
Yu Q et al. "Protective immunity induced by a recombinant BCG vaccine encoding the cyclophilin gene of Toxoplasma gondii", Vaccine, Elsevier, Amsertdam, NL, vol. 31, No. 51, Dec. 2013, pp. 6065-6071.

* cited by examiner

Primary Examiner — Robert A Zeman
(74) Attorney, Agent, or Firm — Forge IP, PLLC

(57) ABSTRACT

Provided is a protein having *Toxoplasma* immunogenicity, the protein being a cyclophilin mutant protein and consisting of the amino acid sequence as shown in SED 2. Further provided is a nucleic acid that may encode a protein having *Toxoplasma* immunogenicity, which has the nucleic acid sequence as shown in SEQ ID NO. 1. Further provided is a vaccine, which is obtained by double-digesting a *Toxoplasma* antigen gene and then linking the same to a prokaryotic expression vector such as pET28a, and transforming the same into a prokaryotic expression engineering strain such as BL21(DE3), thereby inducing the high-efficiency expression thereof, wherein the inducing the high-efficiency expression thereof, wherein the purified protein is a soluble protein which maintains specific immunogenicity thereof.

7 Claims, 5 Drawing Sheets
Specification includes a Sequence Listing.

SEQUENCE LISTING

```
<160> NUMBER OF SEQ ID NOS: 5

<210> SEQ ID NO 1
<211> LENGTH: 489
<212> TYPE: DNA
<213> ORGANISM: Artificial sequence
<220> FEATURE:
<223> OTHER INFORMATION: synthesized

<400> SEQUENCE: 1
atggaaaacg cgggcgtgcg caaagcgtat atggatattg atattgatgg cgaacatgcg      60
ggccgcatta ttctggaact gcgcgaagat attgcgaaaa aaaccgtgaa aaactttatt     120
ggcctgtttg ataaatataa aggcagcgtg tttcatcgca ttattccgga ttttatgatt     180
cagggcggcg attttgaaaa ccataacggc accggcggcc atagcattta tggccgccgc     240
tttgatgatg aaaactttga tctgaaacat gaacgcggcg tgattagcat ggcgaacgcg     300
ggcccgaaca ccaacggcag ccagttttt attaccaccg tgaaaaccga atggctggat     360
gcgcgccatg tggtgtttgg caaaattacc accgaaagct ggccgaccgt gcaggcgatt     420
gaagcgctgg gcggcagcgg cggccgcccg agcaaagtgg cgaaaattac cgatattggc     480
aaaaaagaa                                                              489

<210> SEQ ID NO 2
<211> LENGTH: 163
<212> TYPE: PRT
```

```
<213> ORGANISM: Artificial sequence
<220> FEATURE:
<223> OTHER INFORMATION: synthesized

<400> SEQUENCE: 2

Met Glu Asn Ala Gly Val Arg Lys Ala Tyr Met Asp Ile Asp Ile Asp
1               5                   10                  15

Gly Glu His Ala Gly Arg Ile Ile Leu Glu Leu Arg Glu Asp Ile Ala
                20                  25                  30

Lys Lys Thr Val Lys Asn Phe Ile Gly Leu Phe Asp Lys Tyr Lys Gly
            35                  40                  45

Ser Val Phe His Arg Ile Ile Pro Asp Phe Met Ile Gln Gly Gly Asp
        50                  55                  60

Phe Glu Asn His Asn Gly Thr Gly Gly His Ser Ile Tyr Gly Arg Arg
65                  70                  75                  80

Phe Asp Asp Glu Asn Phe Asp Leu Lys His Glu Arg Gly Val Ile Ser
                85                  90                  95

Met Ala Asn Ala Gly Pro Asn Thr Asn Gly Ser Gln Phe Phe Ile Thr
            100                 105                 110

Thr Val Lys Thr Glu Trp Leu Asp Ala Arg His Val Val Phe Gly Lys
        115                 120                 125

Ile Thr Thr Glu Ser Trp Pro Thr Val Gln Ala Ile Glu Ala Leu Gly
130                 135                 140

Gly Ser Gly Gly Arg Pro Ser Lys Val Ala Lys Ile Thr Asp Ile Gly
145                 150                 155                 160

Lys Lys Glu

<210> SEQ ID NO 3
<211> LENGTH: 6
<212> TYPE: PRT
<213> ORGANISM: Artificial sequence
<220> FEATURE:
<223> OTHER INFORMATION: synthesized

<400> SEQUENCE: 3

His His His His His His
1               5

<210> SEQ ID NO 4
<211> LENGTH: 33
<212> TYPE: DNA
<213> ORGANISM: Artificial Sequence
<220> FEATURE:
<223> OTHER INFORMATION: synthesized

<400> SEQUENCE: 4
atggaattca tggaaaacgc gggcgtgcgc aaa                           33

<210> SEQ ID NO 5
<211> LENGTH: 29
<212> TYPE: DNA
<213> ORGANISM: Artificial Sequence
<220> FEATURE:
<223> OTHER INFORMATION: synthesized

<400> SEQUENCE: 5 aagctttttct tttttgccaa tatcggtaa                              29
```

VACCINE USED FOR PREVENTING TOXOPLASMA GONDII INFECTION AND PREPARATION METHOD THEREFOR

BACKGROUND OF THE INVENTION

Technical Field

The present invention relates to the fields of immunology and biology, particularly to a vaccine for preventing canine *Toxoplasma gondii* infection and a preparing method thereof, and more particularly to the application of the vaccine in preventing canine toxoplasmosis infection.

Background Art

Toxoplasmosis is a multi-host protozoonosis caused by *Toxoplasma gondii* of genus *toxoplasma* in class sporozoa, which is parasitic in animal or human cells. It is a zoonotic parasitic disease worldwide distributing. Cats are definitive host, and humans and various animals are intermediate hosts. *Toxoplasma gondii* has become one of the important public health problems to be solved urgently in China for the following main reasons: (1) The infection rate of *Toxoplasma gondii* to human is extremely high, generally ranging from 20% to 50%, especially among women and children. About one third of people in the world are infected with *Toxoplasma gondii*. The infection rate of *Toxoplasma gondii* in Chinese population is 5% 20%. Vertical transmission occurs in about 50% of pregnant women, whether or not they have clinical symptoms after infection, causing symptoms such as premature delivery, abortion, fetal malformation or stillbirth. Toxoplasmosis is also a complication in 6%~10% AIDS patients. *Toxoplasma gondii* infection causes 50% encephalitis among AIDS patients. (2) *Toxoplasma gondii* infection is very common in domestic animals such as cats, dogs, pigs, sheep, cattle and rabbits, and the infection rate is as high as 10%~50%, resulting in abortion rate of pigs, cattle and sheep reaching 30-40.7%. *Toxoplasma gondii* infection in pigs can also cause "unknown fever", with a mortality rate of 60%. Therefore, toxoplasmosis is one of the important factors causing livestock abortion, which affects animal husbandry production. (3) With the increasing number of pets kept in families, dogs and cats are widely kept as pets. Dog is an important intermediate host of *Toxoplasma gondii*, and cat is the only definitive host, which has become the main source of human toxoplasmosis due to its close contact with people. (4) *Toxoplasma gondii* can infect all nucleated cells, and the average infection rate of animals (pigs, cattle, sheep, chickens, ducks and geese, etc.) is 15.4%. After infection, *Toxoplasma gondii* spreads all over the tissues of the whole body in the form of bradyzoite. As a result, *Toxoplasma gondii* easily flows into the food market through meat, milk and eggs, and becomes a infection source to human, which seriously threatens the public health safety of animal food.

Up to now, there are still no ideal commercial vaccines and drugs for preventing and treating canine toxoplasmosis at home and abroad. *Toxoplasma gondii* infection can cause host protective immune response. Therefore, developing a safe and effective vaccine should be a good preventive measure for toxoplasmosis. The development of *Toxoplasma gondii* vaccine has been centered on whole-worm vaccine since 1960s. Whole-worm vaccine comprises inactivated vaccine and attenuated vaccine, but inactivated vaccine lacks immunoprotection to mice, so it has no practical application value. The virulence of *Toxoplasma gondii* bradyzoites is weakened after being treated with ultraviolet rays, radiation and chemical reagents, which can induce strong immune responses such as Ts-4, T-263 and S48. However, live attenuated vaccines are in danger of insufficient attenuation and reversion of virulence, so attenuated vaccines cannot be widely used. The genetic engineering vaccine of the present invention expresses *Toxoplasma gondii* antigen gene in an efficient expression vector, thereby obtaining a large amount of purified single antigen, which have advantages such as better immunogenicity, higher biological safety and lower immune irritation. Based on the above discussion, it can be found that genetic engineering vaccine gives a hope for *Toxoplasma gondii* vaccine development, and has higher value in development and application.

The development of *Toxoplasma gondii* can be divided into five stages, namely trophozoites, cysts, schizonts, gametophytes and oocysts. The first two stages are carried out in the intermediate host, and the last three stages are only carried out in definitive host, that is, the intestinal tract and body surface of cats. In the development process of worms, cats eat mature oocysts or animal tissues containing *Toxoplasma gondii* cysts, and the sporozoites in the oocysts or trophozoites in the cysts invade the digestive tract of the body, gradually move to intestinal epithelial cells, and present coccidia-type development and reproduction in the cells.

Dogs suffering from toxoplasmosis are often caused by infection due to eating sporulated oocysts or swallowing meat and viscera containing cysts and trophozoites. In addition, infection may occur through damaged skin, respiratory tract, eyes and placenta. Most of the affected dogs are puppies or young dogs less than 1 year old. Pregnant bitches can be infected with toxoplasmosis which causes abortion and premature birth. Adult dogs are mostly recessive or transient, but there are also reports of death. In addition, occurrence of the disease is also related to the dog's bad habit of eating feces or preying on rats. When dogs eat the oocysts discharged from cats, the sporozoites inside invade the cells outside the intestinal tissues through lymph and blood circulation, and propagate in a double-bud way, producing many tachyzoites, which is called an acute infection period. When the body produces immunity, tachyzoites will become bradyzoites and form cysts which will live in the brain, eyes, skeletal muscles and heart for a long time, this period is chronic infection period. Dogs will suffer from acute disease due to high toxicity of *Toxoplasma gondii* if immunity and resistance are not developed. On the contrary, if the reproduction of *Toxoplasma gondii* is hindered, there will be slight disease or no clinical symptoms.

Cyclophilin (CyP) is a cell-soluble protein widely found in prokaryotes and eukaryotes, which is highly conserved in structure. At present, it has been found that CyP exists in *Taenia echinococcus, Filaria malayi, Toxoplasma gondii, Plasmondium falciparum, Neospora caninum, Schistosomiasis japonica, Entamoeba histolytica, Eimeria tenella* and other parasites.

BRIEF SUMMARY OF THE INVENTION

In view of the above problems, the present application provides a recombinant subunit inactivated vaccine for preventing *Toxoplasma gondii* infection in dogs and usage of the vaccine. By using genetic engineering technology, the cyclophilin gene of *Toxoplasma gondii* is cloned and modified, and the modified cyclophilin gene is transferred into engineering bacteria for expression. After induction, the recombinant antigen is highly expressed, and shows good immunogenicity according to physiological studying of the specificity and immunogenicity of the recombinant antigen.

A first object of the application is to provide a protein having *Toxoplasma gondii* immunogenicity, which consists of the amino acid sequence represented by SEQ ID NO. 2. The source of the sequence is as follows: the spatial structure and hydrophobicity of the protein are modified according to the amino acid sequence of cyclophilin protein, and the modified amino acid sequence is codon-optimized by using the codon optimization website http://www.encorbio.com/protocols/Codon.htm for more efficient expression in *Escherichia coli*.

The technical solutions in the present invention to solve the above technical problems are as follows.

A protein having *Toxoplasma gondii* immunogenicity, which is a cyclophilin mutant protein and consists of the amino acid sequence represented by SEQ ID NO. 2.

The protein having *Toxoplasma gondii* immunogenicity may be protein mutant obtained by substituting, deleting or replacing the amino acid sequence represented by SEQ ID NO. 2.

The protein having *Toxoplasma gondii* immunogenicity may be protein consisting of an amino acid sequence with more than 90% homology with the amino acid sequence represented by SEQ ID NO. 2.

The protein having *Toxoplasma gondii* immunogenicity may be a protein consisting of an amino acid sequence with more than 80% homology with the amino acid sequence represented by SEQ ID NO. 2.

A method for preparing the above proteins comprises the following steps: carrying out nuclease digestion corresponding to the SEQ ID NO. 1 or a mutant thereof and then connecting it to a vector, and transforming or transfecting the vector into prokaryotic or eukaryotic cells for expression.

A method for preparing cyclophilin mutant protein comprises the following steps:
(1) cloning related genes into expression vector plasmids to obtain recombinant expression vector;
(2) the recombinant expression vector transforming *Escherichia coli* to obtain genetic engineering bacteria;
(3) carrying out fermentation culture of the genetic engineering bacteria to express cyclophilin mutant protein; and
(4) Recovering the supernatant of the crushed genetic engineering bacteria, and separating and purifying the *Toxoplasma gondii* cyclophilin mutant protein.

In the above method, the vector in step (2) are PET-28a, and *Escherichia coli* is BL21(DE3).

In the above method, the recombinant genetic engineering bacteria in step (2) is DH5α/pET28a-18C.

In the above method, the expression of *Toxoplasma gondii* cyclophilin mutant protein by genetic engineering bacteria in step (3) is constitutive expression.

In the above method, the recombinant *Toxoplasma gondii* cyclophilin mutant protein in step (3) is any one of the following three polypeptides:
1) Polypeptide containing the sequence represented by SEQ ID NO. 2 in the sequence listing;
2) Polypeptide which is at least 80% homologous to the polypeptide of 1);

The invention also provides application of *Toxoplasma gondii* cyclophilin mutant protein in preparation of subunit inactivated vaccine for preventing canine *Toxoplasma gondii* infection.

The invention also provides application of *Toxoplasma gondii* cyclophilin mutant protein in preparing human *Toxoplasma gondii* vaccine and cat *Toxoplasma gondii* vaccine.

A nucleic acid capable of encoding a protein having *Toxoplasma gondii* immunogenicity may be a nucleic acid encoding an amino acid sequence represented by SEQ ID NO. 2, and may have a nucleic acid sequence represented by SEQ ID NO. 1.

The present application also provides a *Toxoplasma gondii* subunit inactivated vaccine, which comprises an amino acid sequence and a mutant thereof represented by claim 1, or a nucleotide sequence and an optimized sequence thereof represented by claim 4, and medically acceptable vector.

The present application also provides an application of the *Toxoplasma* subunit inactivated vaccine in preparing drugs for preventing canine *Toxoplasma gondii* infection. The medicine comprises an amino acid sequence and a mutant thereof represented by claim 1, or a nucleotide sequence and an optimized sequence thereof represented by claim 4, and a medically acceptable vector.

A method for preparing the subunit inactivated vaccine comprises the following steps: connecting *Toxoplasma gondii* antigen to an expression vector, transforming the antigen into prokaryotic expression engineering bacteria, inducing high-efficiency expression thereof, purifying the antigen to obtain soluble fusion protein, and adding vaccine adjuvant therein. The vaccine adjuvant may be MF59 adjuvant or Seibicke 206 adjuvant.

In the vaccine for preventing canine toxoplasmosis, the protein concentration is at least 10 µg/ml to 300 µg/ml.

The concentration of protein in the above vaccine for preventing canine toxoplasmosis is preferably 100 µg/ml.

The prokaryotic expression engineering bacteria may be BL21(DE3),BLR(DE3)pLysS, OrigamiB(DE3), C41(DE3) pLysS, C41(DE3), BL21, AD494, BL21-SI, BL21 trxB (DE3)pLysS, BL21 trxB(DE3), Origami 2(DE3)pLysS, B834(DE3)pLysS, Rosetta-gami B(DE3), Rosetta-gami B(DE3)pLysS, Rosetta-gami(DE3)pLysS, NovaBlue T1, Tuner(DE3)pLacI, Tuner(DE3)pLysS, Tuner(DE3), Tuner, RosettaBlue(DE3)pLys5, RosettaBlue(DE3)pLacI, Rosetta-Blue(DE3), RosettaBlue, Rosetta-gami B(DE3)pLacI, Rosetta-gami B, Rosetta-gami2(DE3)pLacI, Rosetta-gami 2, Rosetta-gami(DE3)pLacI, Rosetta-gami, Rosetta2(DE3) pLacI, Rosetta2(DE3), Rosetta 2, Origami 2(DE3)pLacI, Rosetta(DE3)pLacI, Rosetta, OrigamiB(DE3)pLacI, OrigamiB(DE3)pLysS, Origami B, Origami 2, Origami(DE3) pLacI, Origami(DE3)pLysS, Origami, BL21(DE3)pLacI, BLR, B834(DE3), BLR(DE3), DH10MultiBac, ER2738, ET12567(pUZ8002), BL21-AI, BJ5183, Rosetta-gami 2(DE3)pLysS, Rosetta-gami 2(DE3), Rosetta-gami(DE3), BL21(DE3)pLySs, Rosetta 2(DE3)pLySs, Rosetta(DE3) pLySs, Rosetta(DE3), Origami(DE3), Origami 2(DE3), BL21-Gold(DE3), M15[pREP4], Sure, BL21 Star(DE3) pLySs, BL21 Star(DE3), and engineering bacteria modified based on any of the above engineering bacteria.

The present application also provides a host cell comprising a nucleic acid corresponding to the SEQ ID NO. 1 or a mutant thereof and a biological vector.

A second object of the present application is to provide a vector comprising the nucleotide sequence SEQ ID NO. 1. The vector ispET-28a, pMAL-p5x, pET-42b(+), pCold-GST, pTrcHis A, pGEX-KG, pET-28b(+), pBAD102/D-TOPO, pAmCyan, ptdTomato, pCS105, pET101/D-TOPO, pET-24a(+), pET-24c(+), pET-24d(+), pET-27b(+), pET-25b(+), pET-28c(+), pET-29a(+), pET-29b(+), pET-29c(+), pET-30b (+), pET-30c(+), pET-30 Xa/lIC, pET-30 EK/lIC, pET-31b (+), pET-32b(+), pET-32c(+), pET-32 EK/lIC, pET-32

Xa/lIC, pET-33b(+), pET-39b(+), pET-40b(+), pET-41a(+), pET-41b(+), pET-42c(+), pET-43.1a(+), pET-43.1b(+), pET-43.1c(+), pET-43.1 EK/lIC, pET-43.1 EK/lIC, pET-44a(+), pET-44b(+), pET-44c(+), pET-44 EK/lIC, pET-45b(+), pET-46 EK/lIC, pET-47b(+), pET-48b(+), pET-49b(+), pETDuet-1, pET-37b(+), pET-5b(+), pET-51b(+), pET-52b(+), pBV220, pkk232-8, pET-15b, pQE-16, pCold IV, pQE-70, pSUMO, pET-SUMO, pDsRed-Express2, pColdS-SUMO, pCold TF, pCold III, pCold II, pCold I, pE-SUMO, pCold-ProS2, pBAD202/D-TOPO, pACYC184, pBAD/Thio-TOPO, pBad/Myc-His C, pBad/Myc-His B, pBad/Myc-His A, pBad/His C, pBad/His B, pBad/His A, pBAD-TOPO, pET-23b(+), pET-23a(+), pET-23c(+), pET-23(+), pET-12b (+), pET-12c(+), pET-12a(+), pET-11b(+), pET-11a(+), ET-11c(+), pBad24, pQE-81L, pQE-32, pQE-9, pQE-31, pQE-60, pQE-40, pET-50b(+), pET-26b(+), pET-32a(+), pET-21b(+), pET-22b(+), pET-14b, pET-16b, pET-19b, pET-20b(+), pET-21d(+), pET-21c(+), pET-21b(+), pET-21a(+), pET-30a(+), pGEX-4T-3, pGEX-5X-2, pG-KJE8, pGro7, pCDFDuet-1, pTf16, pEZZ18, pBAD18, pMAL-c5x, pMal-p2E, pMal-p2X, pET-41 EK/lIC, pMal-c4X, pTrcHis B, pET-3b(+), pGEX-3X, pGEX-4T-2, pGEX-4T-1, pTrc99a, pET-His, pALEX a,b,c, pACYC177, pKD4, pKD20, pMXB10, pKJE7, pRSET B, pGEX-2T, pRSFDuet-1, pCO-LADuet-1, pET-3a(+), pGEX-6P-3, pGEX-6P-2, pGEX-6P-1, pGEX-5X-3, pGEX-5X-1, pGEX-2TK, pRSET A, pMal-c2G, pMal-c2E, pMal-c2X, PRSET C and the modified vector based on any of the above vector. The expression vector is preferably pET-28a vector.

A third object of the present application is to provide a soluble fusion protein, the amino acid sequence of which comprises SEQ ID NO. 2 and its mutant.

Preferably, the soluble fusion protein comprises *Toxoplasma gondii* cyclophilin mutant protein and histidine purified label, wherein the DNA sequence encoding *Toxoplasma gondii* cyclophilin mutant protein is selected from SEQ ID NO. 1; and the amino acid sequence of the purified label is SEQ ID NO. 3.

The amino acid sequence of the soluble fusion protein is preferably SEQ ID NO. 2.

A third object of the present application is to provide a host cell containing the above vectors or transformed or transfect with the nucleotide sequence of claim 1.

A fourth object of the present application is to provide a method for preparing a soluble fusion protein, which comprises expressing the soluble fusion protein through a host cell and separating the soluble fusion protein.

A fifth object of the present application is to provide a vaccine comprising the nucleotide sequence in SEQ ID NO. 2 and a medically acceptable vector.

The vaccine is preferably prepared by having *Toxoplasma gondii* antigen double-digested, connected to pET28a expression vector, and then transformed into BL21(DE3) engineering bacteria, induced high-efficient expression thereof, and purified so as to obtain protein which is soluble fusion protein, then adding MF59 adjuvant or Seibicke 206 adjuvant therein. The vaccine keeps its unique immunogenicity and is suitable for industrial production.

The present invention has the following advantages. Antigen genes which are effective for *Toxoplasma gondii* are selected to develop subunit inactivated vaccines. The subunit inactivated vaccine prepared by the antigen has strong cellular immunity and humoral immunity effects, and can induce the innate immune response of the body and secrete various cellular inflammatory factors, thereby effectively preventing canine toxoplasmosis. According to the present application, the sequence of cyclophilin protein is optimized, and the expression amount in prokaryotic cell *Escherichia coli* is twice of that before optimization. The vaccine provided by the present application can be prepared by engineering bacteria and then adding therein vaccine adjuvant. The vaccine can keep its unique keep specific immunogenicity and is suitable for industrial production.

Figure 1:
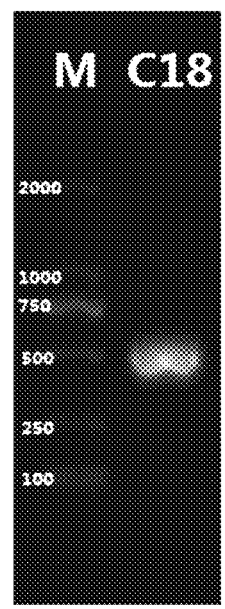
FIG. 1 shows an ORF amplification results of SEQ ID NO. 2 gene.

In the drawing, M is DL2000 marker; C18 is target gene fragment.

Figure 2:
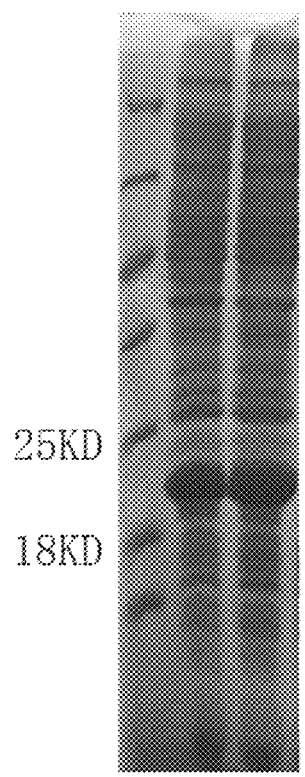

FIG. 2 shows an SDS-PAGE result of *Toxoplasma gondii* cyclophilin protein and *Toxoplasma gondii* cyclophilin mutant protein.

In the drawing, M is protein marker; r1 is soluble expression of *Toxoplasma gondii* cyclophilin protein; r2 is soluble expression of *Toxoplasma gondii* cyclophilin mutant protein.

Figure 3:
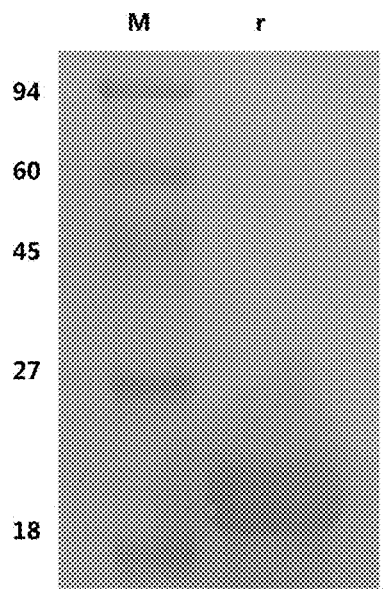

FIG. 3 shows a purified SDS-PAGE result of recombinant mutant expression protein of *Toxoplasma gondii* cyclophilin.

In the drawing, M is protein marker; r is recombinant cyclophilin mutant protein.

Figure 4:
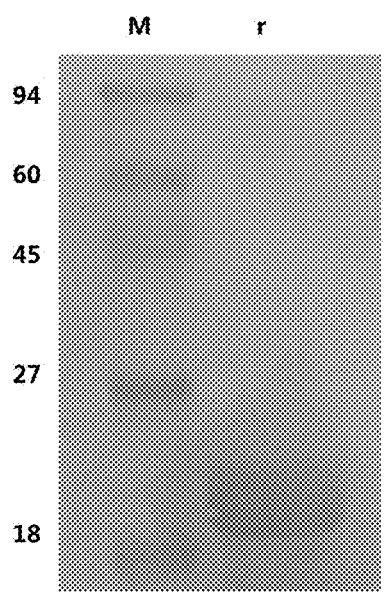

FIG. 4 shows a result of Western-blot identification of the specificity of recombinant protein expressed in vitro.

In the drawing, M is protein marker; r is recombinant cyclophilin mutant protein.

Figure 5:
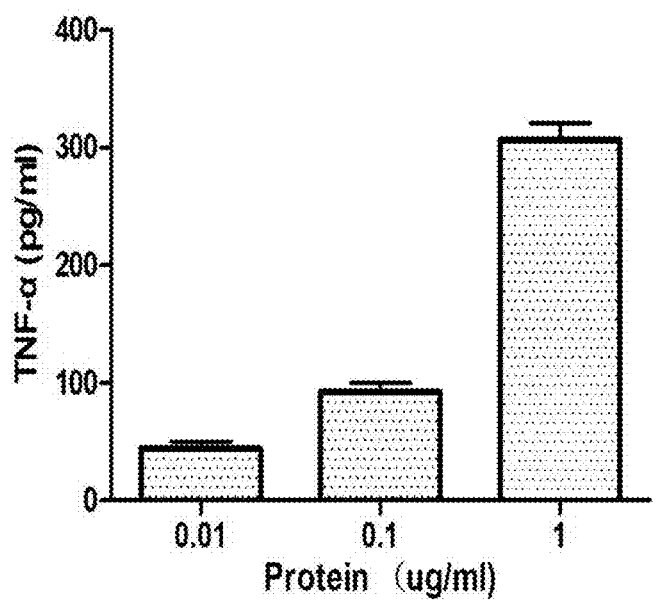

FIG. 5 shows a TNF-α level produced by mouse RAW264.7 cells under the stimulation of *Toxoplasma gondii* cyclophilin recombinant mutant protein.

Figure 6:
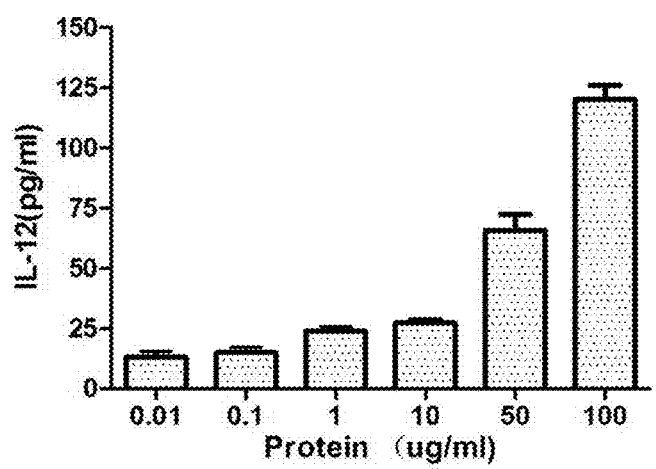

FIG. 6. shows an IL-12 level produced by mouse dendritic cells under the stimulation of *Toxoplasma gondii* cyclophilin recombinant mutant protein.

Figure 7:
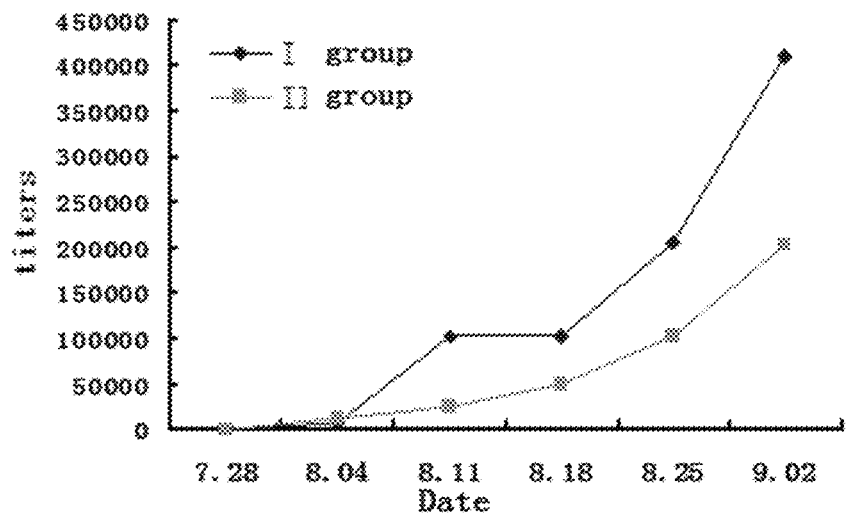

FIG. 7 shows an antibody titer diagram of mouse injected with *Toxoplasma gondii* cyclophilin recombinant mutant protein vaccine.

Figure 8:
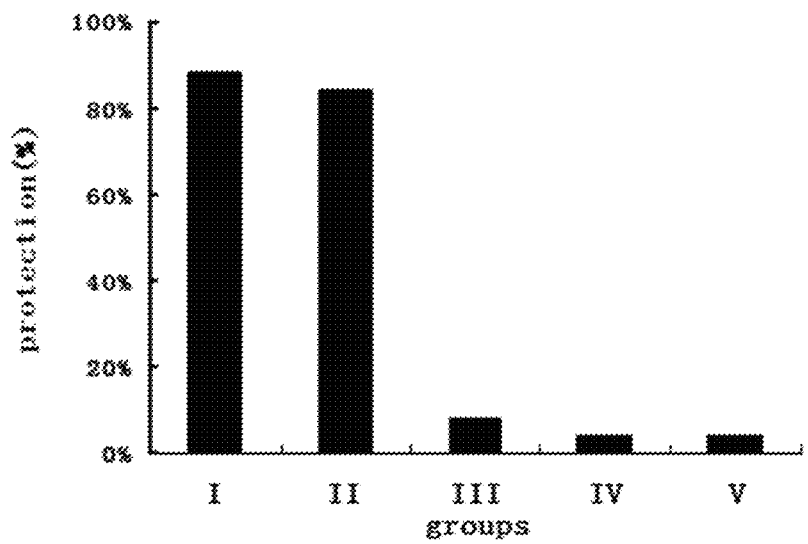

FIG. 8 shows a protective effect of *Toxoplasma gondii* recombinant mutant protein vaccine against *Toxoplasma gondii* infection in mouse.

Figure 9:
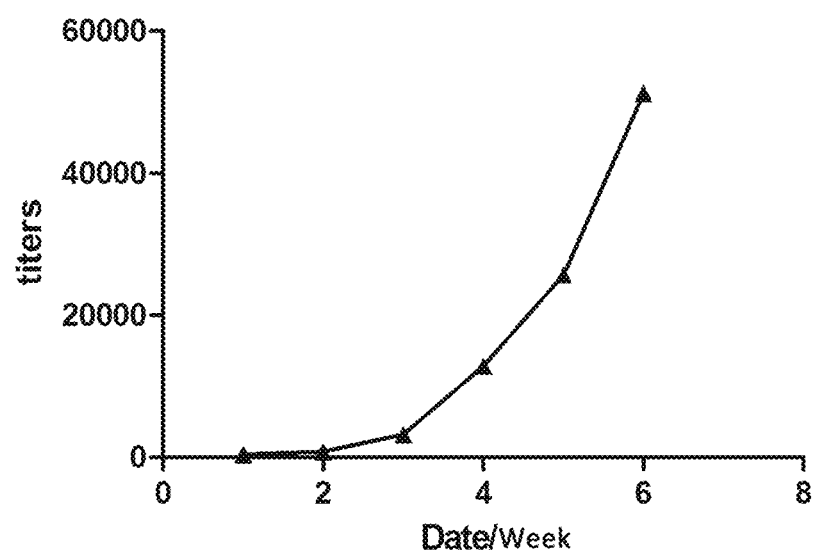

FIG. 9 shows an antibody titer diagram produced by dogs vaccinated with *Toxoplasma gondii* cyclophilin recombinant mutant protein vaccine.

DETAILED DESCRIPTION OF THE INVENTION

The technical solution of the present invention will be represented by detail with examples hereinafter. The described examples are some but not all examples of the present invention. Based on the examples of the present invention, all other examples can be obtained by those skilled in the art without creative effort, all of which fall within the scope of protection of the present invention.

Example 1: Construction of Prokaryotic Expression Vector of *Toxoplasma gondii* Recombinant Cyclophilin Mutant Protein According to the nucleic acid sequence SEQ ID NO. 1, at the same time, according to the physical map of prokaryotic expression vector pET28a, primers were designed and restriction sites were introduced.

Upstream primer: ATGGAATTC ATG-GAAAACGCGGGCGTGCGCAAA

Downstream primer: AAGCTT TTCTTTTTTGC-CAATATCGGTAA

The gene sequence represented by SEQ ID NO. 1 was artificially synthesized, and then amplified by the above primers. The purified PCR product was cloned into pMD-18-T, and then digested and sequencing identified for the positive clone bacteria. The purified target fragment of the positive plasmid was double digested by EcoRI and Hind III, and then connected to the prokaryotic expression vector pET28a. The ligation product was transformed into *E. coli* DH5a competent cells and then the recombinant plasmid was screened. The prokaryotic expression plasmid pET28a-C18 was obtained by double-digesting reaction identification with EcoRI and Hind III. The pET28a-C18 was transformed into BL21(DE3) engineering bacteria, and a single colony was inoculated into 5 ml LB liquid culture medium (containing 100 μg/ml kanamycin), which was cultured overnight at 37° C. and 220 rpm. The amplification results of cyclophilin mutant ORF are shown in FIG. 1.

Example 2: Purification of Expressed Protein (1) Extraction and Solubility Verification of Expressed Protein

*E. coli* BL21(DE3) single colony transformed with recombinant plasmid pET-28a(+)-C18 was selected to be inoculated in 5 ml LB liquid culture medium, and cultured overnight at 37° C. On the next day, the seed solution was transferred to 800 ml LB liquid medium for propagation at 37° C. When OD600 of bacterial liquid is monitored to 0.6~0.7. The expression was induced under the optimum conditions. Bacteria were collected by centrifugation, suspended in 20 ml PBS, frozen and thawed 5 times (−80° C., 1 h/37° C., 10 min), and then treated by ultrasound. The supernatant obtained by centrifugation was soluble protein (active protein). The precipitate was suspended in 10 ml denaturing buffer and shaken for 1 h at room temperature. The supernatant obtained by centrifugation is insoluble protein (denatured protein). SDS-PAGE detection was carried out to verify the solubility of the target protein. If the target protein is mainly located in the supernatant of soluble protein, it is soluble expression. If the target protein is mostly located in the supernatant of insoluble protein, it is expressed as inclusion body. The results showed that the modified *Toxoplasma gondii* cyclophilin mutant protein was soluble, with the expression level of 120 mg/l, while the unmodified cyclophilin protein was soluble (the preparation method is the same as literature: Cloning and Prokaryotic Expression of *Toxoplasma gondii* Cyclophilin Gene, Li Yunna, 2010), with the expression level of 60 mg/l, and the results are shown in FIG. 2.

(2) Purification of Fusion Expressed Protein

Balance the nickel column to stable status with solution A (PBS), and flush the system with solution A at a flow rate of 20 ml/min for 2 min. Connect the balanced nickel column to the sample loading interface, and flow through the sample at a flow rate of 1 ml/min to make the target protein hang on the column. After the flow-through, connect the nickel column with the target protein to the elution interface. At first, the nickel column was balanced with solution A at a flow rate of 1 ml/min, and the unbound foreign proteins were washed away. Keep the flow rate constant and set gradient impurity washing conditions. The concentration of B solution (PBS, containing 1 M imidazole) is 10%, that is, the concentration of imidazole is 100 mM, and time is 30 min, and the nonspecific adsorbed foreign protein is washed away. Keep the flow rate constant and set the elution conditions. The concentration of B solution is 30%, that is, the imidazole concentration is 300 mM, time is 120 min, the target protein is eluted, and the purity of the collected target protein is observed by SDS-PAGE. The results are shown in FIG. 3. The results of identifying the specificity of recombinant mutant protein expressed in vitro by Western-blot are shown in FIG. 4.

Example 3: Detection of Immunogenicity of the Expression Product on Mouse Macrophage The RAW264.7 cells were inoculated into a 24-well culture plate at $0.5 \times 10^6$/ml, each well was cultured at 37° C. for 24 hours with 0.5 ml of 5% $CO_2$. The recombinant cyclophilin mutant protein of *Toxoplasma gondii* was dissolved in RAW264.7 cell culture medium after the supernatant was sucked out. According to the concentration of 1 μg/ml, 0.1 μg/ml, 0.01 μg/ml, was added to the 24-well plate at an amount of 0.5 ml/well, and the same volume of PBS was used as negative control. The cell culture plate was cultured in an incubator with 5% $CO_2$ and 37° C. for 48 hours. The supernatant was collected and the TNF-α level was detected by ELISA. The results showed that the production of TNF-α increased with the increase of protein concentration, ranging from 40 pg to 310 pg. The results are shown in FIG. 5. Therefore, *Toxoplasma gondii* recombinant cyclophilin mutant protein can stimulate RAW264.7 cells to produce TNF-α.

Example 4: Detection of Immunogenicity of Expression Product on Mouse Dendritic Cells The mouse dendritic cells were isolated, the cell concentration was adjusted to $0.5 \times 10^6$ cells/ml, and then inoculated into a 24-well tissue cell culture plate with 0.5 ml per well. The treated recombinant cyclophilin mutant protein of *Toxoplasma gondii* was added into the cell culture plate at the concentrations of 100 μg/ml, 50 μg/ml, 10 μg/ml, 1 μg/ml, 0.1 μg/ml and 0.01 μg/ml per well, respectively, with an amount of 0.5 ml per well. The cell culture plate was cultured in an incubator with 5% $CO_2$ and 37° C. for 24 hours, and the supernatant was collected. The level of IL-12 in the supernatant was detected by ELISA. The results show that the content of IL-12 produced by each group is protein concentration dependent, that is, it increases with the increase of protein concentration, and the results are shown in FIG. 6. The results indicated that *Toxoplasma gondii* recombinant cyclophilin mutant protein could stimulate mouse dendritic immune cells to produce a large amount of IL-12.

Example 5: Immune Challenge and Protection Experiment of *Toxoplasma gondii* Recombinant Subunit Vaccine in Mice 125 female SPF BALB/c mice aged from 8 to 10 weeks were divided into 5 groups with 25 mice in each group. The first group was cyclophilin experimental group I (adjuvant is MF59, 30 μg per mouse, subcutaneous injection), the second group was cyclophilin experimental group II (adjuvant 206, 30 μg per mouse, subcutaneous injection), the third group was negative control group I (equal volume PBS with adjuvant MF59, subcutaneous injection), the fourth group was negative control group II (equal volume PBS, with adjuvant 206, subcutaneous injection), and the fifth group was blank control group II (equal volume PBS, subcutaneous injection). Injection was conducted three times for each group at an interval of two weeks. Antibody titers were detected weekly. One week after the third immunization, 103 purified *Toxoplasma gondii* trophozoites were injected intraperitoneally into every mouse, and the status of mice was observed and recorded every day.

The antibody results showed that the antibody level increased rapidly three weeks after immunization, and reached its peak at six weeks, and FIG. 7 shows the titer of vaccine antibody.

The results of immune protection test showed that the immune survival rate of experimental group was significantly better than that of negative control group and blank control group, and the effect of MF59 adjuvant vaccine group was better than that of 206 adjuvant vaccine group (see FIG. 8).

Example 6: Experimental Study on Immune Challenge Protection Rate of *Toxoplasma gondii* Recombinant Subunit Vaccine in Dogs Twenty experimental dogs (beagle dogs, sexually mature bitches) without pathogens (including parasitic diseases, viral diseases and bacterial infectious diseases) were selected, especially those without infectious pathogens such as *Toxoplasma gondii, neospora*, canine distemper, canine infectious hepatitis and parvovirus. The experimental animals were divided into two groups. The first group was cyclophilin experimental group (adjuvant MF59, 300 μg/animal, injected subcutaneously), with 15 dogs in total. The second group was a blank control group (PBS of equal volume, injected subcutaneously), with 5 dogs in total. Injection was conducted three times for each group at an interval of two weeks. Antibody titers were detected weekly.

One week after the third immunization, 104 purified *Toxoplasma gondii* trophozoites were injected intraperitoneally. After 30 days, all dogs were dissected, and the infection of *Toxoplasma gondii* in brain, heart, liver, spleen, lung, kidney, lymph node, masseter muscle, tongue muscle and abdominal muscle was detected by PCR. If the PCR results of any tissues were positive, the dog was judged as *Toxoplasma gondii* infected. If the PCR results of all tissues are negative, it is judged as *Toxoplasma gondii* protection.

The antibody results showed that the antibody level of the immune group continued to rise after the first immunization, and the titer of the vaccine antibody was shown in FIG. 9.

After challenge, the results showed that all dogs in the control group were diagnosed as *Toxoplasma gondii* infection, 13 dogs in the immune group were diagnosed as *Toxoplasma gondii* protection, and 2 dogs were diagnosed as *Toxoplasma gondii* infection, indicating a protection rate of 86%.

Based on the above experimental results, the *Toxoplasma* subunit inactivated vaccine provided by the present application has high immune protection rate against *Toxoplasma gondii* in dogs, and can be used as a candidate vaccine for prevention and treatment of *Toxoplasma gondii* in dogs.

Finally, it should be noted that, the above embodiments are provided to describe the technical solutions of the disclosure, but are not intended as a limitation. Although the disclosure has been represented by detail with reference to the embodiments, those skilled in the art will appreciate that the technical solutions represented by the foregoing various embodiments can still be modified, or some technical features therein can be equivalently replaced. Such modifications or replacements do not make the essence of corresponding technical solutions depart from the spirit and scope of technical solutions embodiments of the disclosure.

What is claimed is:

1. A protein having *Toxoplasma gondii* immunogenicity, wherein the protein is a mutant cyclophilin protein comprising the amino acid sequence represented by SEQ ID NO. 2.

2. A nucleic acid encoding the protein having *Toxoplasma gondii* immunogenicity of claim 1, wherein the amino acid sequence represented by SEQ ID NO. 2 is encoded.

3. A host cell, comprising the nucleic acid of claim 2, and a biological vector.

4. The host cell of claim 3, wherein the nucleic acid has the nucleotide sequence represented by SEQ ID NO. 1.

5. The nucleic acid of claim 2, wherein the nucleic acid has the nucleotide sequence represented by SEQ ID NO. 1.

6. A soluble fusion protein, comprising the protein having *Toxoplasma gondii* immunogenicity of claim 1 and a purified label.

7. The protein of claim 6, wherein the amino acid sequence of the purified label is shown in SEQ ID NO. 3.

* * * * *